United States Patent [19]

Cifuentes et al.

[11] Patent Number: 5,389,364
[45] Date of Patent: Feb. 14, 1995

[54] CONDITIONING HAIR WITH AMINOSILANE REACTION PRODUCTS WITH LACTONES OR CARBONATES

[75] Inventors: Martin E. Cifuentes; Patricia A. Giwa-Agbomeirele, both of Midland, Mich.

[73] Assignee: Dow Corning Corporation, Midland, Mich.

[21] Appl. No.: 102,927

[22] Filed: Aug. 6, 1993

[51] Int. Cl.⁶ .......................... A61K 7/06; A61K 7/09
[52] U.S. Cl. .................................. 424/70.122; 424/71
[58] Field of Search .................................. 424/70, 71

[56] References Cited

U.S. PATENT DOCUMENTS

| | | | |
|---|---|---|---|
| 3,817,894 | 6/1974 | Butler et al. | 260/29.2 |
| 5,106,613 | 4/1992 | Hartnett et al. | 424/71 |
| 5,126,126 | 6/1992 | Varaprath et al. | 424/71 |
| 5,174,813 | 12/1992 | Cifuentes et al. | 106/3 |
| 5,240,698 | 8/1993 | Traver et al. | 424/71 |
| 5,269,951 | 12/1993 | McVie et al. | 528/38 |

*Primary Examiner*—G. S. Kishore
*Assistant Examiner*—Peter F. Kulkosky
*Attorney, Agent, or Firm*—James L. DeCesare

[57] ABSTRACT

Hair is conditioned by applying to the hair an effective amount of a composition which includes as the hair conditioning agent, from 0.5 to 5.0 percent by weight of a derivatized amine functional organosilicon compound which is one of (i) a reaction product of an amine functional polysiloxane and a derivative of carbonic acid; (ii) a reaction product of an amine functional polysiloxane and a lactone; (iii) a reaction product of an amine functional silane and a derivative of carbonic acid; or (iv) a reaction product of an amine functional silane and a lactone.

5 Claims, No Drawings

CONDITIONING HAIR WITH AMINOSILANE REACTION PRODUCTS WITH LACTONES OR CARBONATES

BACKGROUND OF THE INVENTION

This invention is directed to certain derivatized amine functional organosilicon compounds which have been found to possess the capability of imparting conditioning benefits to the hair.

Hair preparations are compositions which are employed on the scalp or hair. The most important hair preparations are shampoos, conditioning products, colorants, hairstyling preparations including setting lotions and hairsprays, and permanent wave preparations.

Shampoos are mild cosmetic products for cleaning the hair and scalp. Hair becomes soiled due to skin flakes, sebum, perspiration, dust, and residues from sprays, lotions and conditioning agents. Shampoos are designed to leave the hair clean, pliable, lustrous, possessing a pleasant odor, and easy to untangle, comb, manage, and style.

The principal ingredient of a shampoo is a surfactant which functions to release dirt from the hair and to transport it to the aqueous medium. Since consumers equate lathering with cleanliness, anionic surfactants such as alkyl sulfates and sulfonates are preferred because of their high lather. Numerous other constituents are included in shampoos such as thickeners to prevent the shampoo from running down the face into the eyes, opacifiers to provide a rich pleasing pearlescent appearance, buffers to adjust the pH of the shampoo to a value which is gentle to the skin, and fragrances to impart a pleasant aroma to the washed hair following rinsing. Most frequently, shampoos are marketed as clear products although gels having a higher viscosity and packaged in tubes, and pearlescent compositions are available.

With the advent of consumer trends toward daily hair washing, conditioning shampoos have emerged which are designed to render the hair easy to comb and tangle free in the wet state, as well as glossy and soft when dry. Such conditioning is provided by cationic polymers which upon rinsing product a thin film on the hair. This film functions as a lubricant when the hair is wet and prevents static charge and "flyaway" when the hair is dry.

Conditioning may also be provided by hair conditioning products designed solely for that purpose such as rinses, mousses, aerosols, and pump sprays, which conditions are applied following shampooing. These conditioning products are rinsed from the hair a short time following their application. Such conditioners prevent excessive split ends and other mechanical hair damage and roughening, and seek to neutralize the adverse effects which hair undergoes due to humidity, temperature, exposure to sunlight, frequent washing, combing, and brushing, and cosmetic treatments such as bleaching, dyeing, and waving.

Conditioning is the aspect of hair treatment of focus in the present invention, and conditioning is provided herein by certain reaction products of amine functional polysiloxane or silanes with certain derivatives of carbonic acid or certain lactones.

SUMMARY OF THE INVENTION

The invention relates to a method and to a composition for conditioning hair. According to the invention, hair is conditioned by applying an effective amount of a composition which contains as the hair conditioning agent, from 0.5 to 5.0 percent by weight based on the weight of the hair conditioning composition of a derivatized amine functional organosilicon compound. Suitable derivatized amine functional organosilicon compounds can be either one of (i) a reaction product of an amine functional polysiloxane and a derivative of carbonic acid; (ii) a reaction product of an amine functional polysiloxane and a lactone; (iii) a reaction product of an amine functional silane and a derivative of carbonic acid; or (iv) a reaction product of an amine functional silane and a lactone.

These and other features, objects, and advantages, of the herein described present invention, will become more apparent when considered in light of the following detailed description thereof.

DETAILED DESCRIPTION OF THE INVENTION

In accordance with the invention, a derivatized amine functional organosilicon compound is used as a conditioning agent for hair. The conditioning agent can be one of (i) a reaction product of an amine functional polysiloxane and a derivative of carbonic acid; (ii) a reaction product of an amine functional polysiloxane and a lactone; (iii) a reaction product of an amine functional silane and a derivative of carbonic acid; or (iv) a reaction product of an amine functional silane and a lactone.

A suitable amine functional polysiloxane which can be employed to prepare the reaction product has the formula $$R_{3-z}'Q_xSiO[R_2'SiO]_{x}[R^aQSiO]_ySiQ_zR_{3-z}' \quad (I)$$

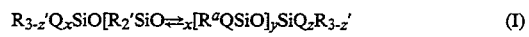

in which R' is an alkyl group of 1 to 4 carbons or a phenyl group with the proviso that at least 50 percent of the total number of R' groups are methyl. $R^a$ is R' or an alkoxy group such as methoxy or ethoxy. Q denotes an amine functional substituent of the formula —R"Z wherein R" is a divalent alkylene radical of 3 to 6 carbon atoms, and Z is a monovalent radical such as —NR$_2$''', and —NR'''(CH$_2$)$_n$NR$_2$'''. R''' is hydrogen or an alkyl group of 1 to 4 carbons. The integer n has a positive integer value of from 2 to 6. The integer z has a value of 0 or 1. The integer x has an average value of 15 to 3000. The integer y has an average value of 0 to 100 when z is 1, y has an average value of 1 to 100 when z is 0; with the proviso that in all cases y has an average value that is not greater than one tenth the average value of x.

Suitable R' groups are methyl, ethyl, propyl, isopropyl, butyl, isobutyl, and phenyl, with the proviso that at least fifty percent of the R' groups are methyl.

The alkylene radicals represented by R" include trimethylene, tetramethylene, pentamethylene, —CH$_2$CHCH$_3$CH$_2$—, and —CH$_2$CH$_2$CHCH$_3$CH$_2$—. Siloxanes where R" is a trimethylene or an alkyl substituted trimethylene radical such as —CH$_2$CHCH$_3$CH$_2$—, are preferred.

Alkyl groups of 1 to 4 carbon atoms as represented by R''' include methyl, ethyl, propyl, isopropyl, butyl, and isobutyl.

Useful Z radicals include the unsubstituted amine radical —NH$_2$, alkyl substituted amine radicals such as —NHCH$_3$, and —NHCH$_2$CH$_2$CH$_2$CH$_3$; and aminoalkyl substituted amine radicals such as —NHCH$_2$CH$_2$NH$_2$, —NH(CH$_2$)$_6$NH$_2$, and —NHCH$_2$CH$_2$CH$_2$N(CH$_3$)$_2$.

When z is zero, the silicon polymer has only pendent amine functional substituents in the polymer chain. When z is one, the silicon polymer may have only terminal amine functional substituents or both terminal and pendent amine functional substituents in the polymer chain. Preferably, x may vary from a value of 25 to 100, and y may vary from zero to 100 when z is one and from one to 100 when z is zero. Most preferably, the value of x+y is in the range of about 50 to 500.

Another suitable amine functional polysiloxane which can be employed has the formula

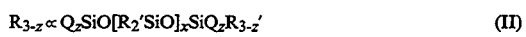

$$R_{3-z}\alpha Q_zSiO[R_2'SiO]_xSiQ_zR_{3-z}' \qquad (II)$$

in which R', Q, x, and z, are the same as noted above the Formula (I), except that in the case of Formula (II), at least one R' group is an alkoxy group of the four carbon atoms such as methoxy or ethoxy radicals.

In either instance, the amine functional polysiloxane of Formula (I) and Formula (II) which is employed in preparing the reaction product, may vary in viscosity, degree of polymerization, and in the mole percent of amine present in the molecule. Generally, a degree of polymerization of about 30 to 400 is sufficient, with a degree of polymerization of about two hundred, being especially preferred for the present invention. The degree of polymerization or DP is the sum of the integers x and y plus two.

The amine functional silane has the formula

$$(RO)_{3-a}R_aSiR'NHR'' \qquad (III)$$

in which R is an alkyl group having one to four carbon atoms. R' in an alkylene group having three to eighteen carbon atoms. R'' is a hydrogen atom, hydrocarbon radicals free of aliphatic unsaturation having one to six carbon atoms, or an aminoalkyl radical having two to six carbon atoms. The value of a is zero or one.

Representative amine functional silanes are compounds having the formula (CH$_3$O)$_3$Si(CH$_2$)$_3$NHCH$_2$CH$_2$NH$_2$, (CH$_3$O)$_3$SiCH$_2$CH$_2$CH$_2$NH$_2$, (C$_2$H$_5$O)$_3$SiCH$_2$CH$_2$CH$_2$NH$_2$, or (CH$_3$O)$_3$SiCH$_2$CH(CH$_3$)CH$_2$NHCH$_2$CH$_2$NH$_2$. Such compounds are described for example in U.S. Pat. No. 3,817,894 issued Jun. 18, 1974.

The derivative of carbon acid is a compound such as ethylene carbonate or propylene carbonate.

The lactone is a compound such as propiolactone, butyrolactone, valerolactone, or caprolactone.

The hair treating compositions of the present invention may contain a surfactant such as an anionic, amphoteric, nonionic, or cationic emulsifying agent, and mixtures of such emulsifying agents. The surfactant should provide an acceptable level of foam on the air and be capable of cleaning the hair.

Suitable anionic surfactants include sulfonated and sulfated alkyl, aralkyl, and alkaryl anionic detergents such as alkyl succinates, alkyl sulfosuccinate, and N-alkyl sarcosinates. Representative detergents are the sodium, magnesium, ammonium, and the mono-, di-, and triethanolamine salts of alkyl and aralkyl sulfates, as well as the salts of alkaryl sulfonates. The alkyl groups of the detergents should have a total of from twelve to about twenty-one carbon atoms, and may be unsaturated. Fatty alkyl groups are preferred. The sulfates may be sulfate ethers containing one to ten ethylene oxide or propylene oxide units per molecule, with two to three ethylene oxide units being sufficient for most purposes.

Typical anionic detergents are sodium lauryl sulfate, sodium lauryl ether sulfate, ammonium lauryl sulfate, triethanolamine lauryl sulfate, sodium C14–16 olefin sulfonate, ammonium C12–15 pareth sulfate, sodium myristyl ether sulfate, ammonium lauryl ether sulfate, disodium monooleamidosulfosuccinate, ammonium lauryl sulfosuccinate, sodium dodecylbenzene sulfonate, triethanolamine dodecylbenzene sulfonate, and sodium N-lauryol sarcosinate.

Among the various surfactants classified as ampholytic or ampholytic which may be used are cocoamphocarboxyglycinate, cocoamphocarboxypropionate, cocobetaine, N-cocamidopropyldimethylglycine, and N-lauryl-N-carboxymethyl-N-(2-hydroxyethyl)ethyenediamine. Other suitable amphoteric detergents which may be used include betaines and sultaines.

Betaines may have the formula R'R''R'''N+(CH$_2$)$_m$COO$^-$ in which R' is an alkyl group having twelve to eighteen carbon atoms and mixtures thereof; R'' and R''' are lower alkyl groups of one to three carbon atoms; and m has a value of one to four. Specific compounds may include alpha-(tetradecyldimethylammonio)acetate, beta-(hexadecyldiethylammonio)propionate, and gamma-(dodecyldimethylammonio)butyrate.

Sultaines may have the formula R'R''R'''N+(CH$_2$)$_m$SO$_3^-$ in which R', R'', R''', and m, are the same as defined above. Specific compounds may include 3-(dodecyldimethylammonio)propane-1-sulfonate, and 3-(tetradecyldimethylammonio)ethane-1-sulfonate.

Nonionic surfactants suitable for use in the hair treating compositions of the present invention can be fatty acid alkanolamides and amine oxide surfactants. Representative fatty acid alkanolamides include fatty acid diethanolamides such as isostearic acid diethanolamide, lauric acid diethanolamide, capric acid diethanolamide, coconut fatty acid diethanolamide, linoleic acid diethanolamide, myristic acid diethanolamide, oleic acid diethanolamide, and stearic acid diethanolamide. Suitable fatty acid monoethanolamides include coconut fatty acid monoethanolamide. Fatty acid monoisopropanolamides which may be used are oleic acid monoisopropanolamide and lauric acid monoisopropanolamide.

Amine oxide nonionic surfactants suitable for use in the present invention are N-alkyl amine oxides such as N-cocodimethylamine oxide, N-lauryl dimethylamine oxide, N-myristyl dimethylamine oxide, and N-stearyl dimethylamine oxide. Suitable N-acyl amine oxides are N-docoamidopropyl dimethylamine oxide and N-tallowamidopropyl dimethylamine oxide. N-alkoxyalkyl amine oxides such as bis(2-hydroxyethyl) C12–15 alkoxy-propylamine oxide may also be employed. The hydrophobic portion of the amine oxide surfactant should be provided by a fatty hydrocarbon chain of about ten to twenty-one carbon atoms.

Cationic surfactants useful in the compositions of the present invention may include those compounds which contain amino or quaternary ammonium hydrophilic moieties in the molecule which are positively charged, such as quaternary ammonium salts. Representative of the various quaternary ammonium salts which may be employed are ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride.

The hair treating compositions of the invention may contain other adjuvants to provide a product which is aesthetically pleasant to the consumer such as thickeners, perfumes, colorants, electrolytes, pH control agents, foam boosters and builders, foam stabilizers, antimicrobials, antioxidants, ultraviolet light absorbers, pearlescent agents such as ethylene glycol monostearate and ethylene glycol distearate, and medicaments.

Thickeners are used to facilitate the hand application of the composition to the hair, and are added in sufficient quantities to provide a more luxurious effect. Hair care compositions which viscosities in the range of three thousand to six thousand centistokes measured at ambient temperature are generally sufficient. Representative thickening agents which may be used are sodium alginate; gum arabic; guar gum; hydroxypropyl guar gum; cellulose derivatives such as methylcellulose, hydroxypropyl methylcellulose; hydroxyethylcellulose, and hydroxypropylcellulose; starch and starch derivatives such as hydroxyethylamylose and starch amylose; locust bean gum; electrolytes such as sodium chloride and ammonium chloride; saccharides such as fructose and glucose; and derivatives of saccharides such as PEG-120 methyl glucose dioleate.

Only cosmetically acceptable perfumes and fragrances should be used to prepare the composition. Colorants may be added where it is desired to confer a hue to the composition. An acid may be employed to adjust the pH within the range of about five to nine. Any water soluble carboxylic acid or mineral acid may be employed. Suitable compounds include mineral acids such as hydrochloric acid, sulfuric acid, and phosphoric acid; monocarboxylic acids such as acetic acid, lactic acid, and propionic acid; and polycarboxylic acids such as succinic acid, adipic acid, and citric acid.

Additional conditioners may be added to the composition in the form of organic cationic conditioning agents for the purpose of providing hair grooming. Such cationic conditioning agents may include quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats Polyquaternium-7, Polyquaternium-8, Polyquaternium-10, Polyquaternium-11, and Polyquaternium-23.

Cationic surfactants such as cetyl trimethylammonium chloride, cetyl trimethylammonium bromide, and stearyltrimethylammonium chloride, may also be employed in the compositions as a cationic conditioning agent.

A preservative may be required and representative compounds which may be employed include formaldehyde, DFMDM hydantoin, 5-bromo-5-nitro-1,3-dioxane, methyl paraben, propyl paraben, sorbic acid, diazolidinyl urea, and imidazolidinyl urea.

The following examples are set forth for the purpose of illustrating methods for preparing derivatized amine functional organosilicon compounds which can be used as hair conditioning agents.

EXAMPLE I

Three hundred grams of a trimethylsilyl-endcapped dimethylsiloxane copolymer having an average degree of polymerization of four hundred and containing two Mole % MeRSiO where $R=-CH_2CH(CH_3)CH_2NH(CH_2)_2NH_2$, was combined and reacted with 16.0 grams of propylene carbonate to produce a high viscosity derivatized fluid of approximately 11,720 centipoise.

EXAMPLE 2

Selected aminosilicone fluids corresponding to Formula (I) and having different degrees of polymerization containing two Mole % pendant R groups where $R=CH_2CH(CH_3)CH_2NHCH_2CH_2NH_2$ were combined with propylene carbonate according to the proportions in Table 1. The mixtures were allowed to react for at least 24 hours while being constantly dispersed on a mixing wheel.

TABLE 1

| Sample | Amino-Silicone | Wt. Amino-Silicone (gm) | Wt. Propylene Carbonate (gm) |
|---|---|---|---|
| I | A | 250.4 | 13.60 |
| II | A | 250.6 | 6.84 |
| III | A | 250.0 | — |
| IV | B | 300.0 | 15.99 |
| V | B | 300.11 | 8.18 |
| VI | B | 300.0 | |

Aminosilicone A — Trimethylsilyl-endblocked; DP (avg.) = 100
Aminosilicone B — Trimethylsilyl-endblocked; DP (avg.) = 400

EXAMPLE 3

Approximately 200.02 grams of a trimethylsilyl-endcapped amine-functional polymer corresponding to Formula (I) and having an average degree of polymerization of 50; 2 Mole % pendant R groups where $R=CH_2CH(CH_3)CH_2NHCH_2CH_2NH_2$ was combined with 10.82 grams of propylene carbonate. The mixture was dispersed using a mixing wheel and allowed to react for approximately 16 hours.

EXAMPLE 4

Approximately 3.3 grams of beta-butyrolactone was combined and reacted with the reaction product of 10.2 parts of methyltrimethoxysilane, 15.2 parts of aminoethylaminopropyltrimethyoxysilane, and 74.6 parts of a silanol endblocked polydimethylsiloxane fluid having a viscosity of forth centistokes.

After mixing for approximately 15 minutes at room temperature, the viscosity of the solution was measured using a Brookfiled LVT Viscometer and determined to be approximately 88 cps. The mixture was allowed to stir overnight. The viscosity of the product did not change with the additional time given to react. An additional 3.3 grams of 'beta'-butyrolactone was added to the product and the mixture was allowed to mix and react overnight. The viscosity of the resultant product was measured and determined to be 162.5 cps. indicating that further reaction had taken place.

EXAMPLE 5

Approximately 23.42 grams of propylene carbonate was combined and reacted with 50 grams of an amine-functional silane $RSi(OR')_3$ where $R=CH_2CH_2CH_2NHCH_2CH_2NH_2$ and $R'=CH_3$. A mild exotherm was noted during the reaction. After mixing overnight at ambient temperature, the viscosity was measured using a Brookfield LVT Viscometer. The viscosity of the product was determined to be 1125 cps. compared to 10 cps. for the mixture initially.

EXAMPLE 6

Approximately 46.8 grams propylene carbonate was combined and reacted with 50 grams of an amine-functional silane $RSi(OR')_3$ where $R=CH_2CH_2CH_2NHCH_2CH_2NH_2$ and $R'=CH_3$. A mild exotherm was noted during the reaction. After mixing overnight at ambient temperature the viscosity was measured using a Brookfield LVT Viscometer. The viscosity of the resultant product was determined to be 237.5 cps., compared to 10 cps. for the mixture initially.

While the reaction products of Examples 1-6 are described in U.S. Pat. No. 5,174,813 issued Dec. 29, 1992, the '813 patent does not teach their use as conditioning agents for the treatment of human hair. Rather, the '813 patent is directed to polish formulations for application to motor vehicles, boats, navigable crafts, wood surfaces, plastic surfaces, and fiber surfaces. Such formulations contain abrasive materials; toxic solvents such as naphtha, Stoddard solvent, mineral spirits, and kerosene; and corrosion inhibitors; which would certainly not suggest their use in applications intended for the care of the human body.

Shampoos in accordance with the present invention can be prepared by combining (i) 3 to 30 percent by weight of an anionic surfactant, measured on a solids basis; (ii) a secondary surfactant such as a nonionic emulsifier in an amount of 2 to 10 percent by weight; (iii) water in an amount of 50 to 93 percent by weight; (iv) the silicone conditioning agent in an amount of 0.5 to 5 percent by weight; (v) one or more thickening agents in an amount to provide a product having a viscosity of 3,000 to 6,000 centistokes; (vi) a pH adjusting amount of an acid in an amount necessary to establish a pH of 4-7; and (vii) the balance of the shampoo being other adjuvants such as preservatives, perfumes, colorants, and dyes, among others, if desired.

The following additional examples are set forth for the purpose of illustrating the use of the derivatized amine functional organosilicon compounds as hair conditioning agents.

EXAMPLE 7

A "control" shampoo was employed for comparison. The control selected was a non-silicone containing shampoo product sold in the consumer market under the trademark PRELL ®. PRELL ® is manufactured and distributed by The Procter & Gamble Company of Cincinnati, Ohio USA. PRELL ® Shampoo contains water, ammonium laureth sulfate, ammonium lauryl sulfate, Cocamide DEA, ammonium xylenesulfonate, sodium phosphate, a fragrance, disodium phosphate, sodium chloride, EDTA, benzophenone-2, methylchloroisothiazolinone, methylisothiazolinone, D & C Green No. 8, and FD & C Blue No. 1.

EXAMPLE 8

A silicone containing shampoo was prepared for comparison with PRELL ® shampoo. The silicone containing shampoo according to the present invention included 62.75 percent by weight of distilled water; 2.0 percent by weight of a polyol alkoxy ester used as a thickening agent and a product sold under the tradename CROTHIX by Croda Inc. of Parsippany, N.J. USA; 3.0 percent by weight of the nonionic surfactant Cocamide DEA which was a product sold under the tradename MONAMIDE 1159 by Mona Industries Inc. of Paterson, N.J. USA; 2.0 percent by weight of the derivatized amine functional polysiloxane of the invention; 30.0 percent by weight of the anionic surfactant ammonium lauryl sulfate containing 30.0 percent by weight of the active ingredient, and product sold under the tradename STANDAPOL A by Henkel Corp./Emery Grp. Cospha/CD of Ambler, Pa. USA; a sufficient amount of a 50.0 percent citric acid solution to adjust the pH to 5.5 to 6.0; a sufficient amount of ammonium chloride to provide a final shampoo viscosity of 3,000 to 6,000 centistokes; and 0.25 percent by weight of the preservative DMDM Hydantoin which is a product sold under the trademark GLYDANT ® by Lonza Inc. of Fairlawn, N.J. USA.

EXAMPLE 9

The shampoo of Example 8 was prepared by adding water and CROTHIX to a 250 milliliter beaker, heating the beaker to 65-73 degrees Centigrade, and mixing the ingredients for ten minutes. MONAMIDE 1159 was added to the beaker and the contents were mixed for ten minutes. The silicone conditioning agent was added and mixed in the beaker for ten minutes, followed by the addition of STANDPOL A. Mixing was continued. GLYDANT ® was added to the beaker after the beaker had been removed from the heating source and allowed to cool to ambient temperature. The pH of the shampoo was adjusted to 5.5 to 6.0 with citric acid, and ammonium chloride was added to make a final adjustment of the final shampoo viscosity. Any water lost during the process due to evaporation was supplemented.

EXAMPLE 10

Five silicone containing shampoos were prepared according to Examples 8 and 9 for comparison with the non-silicone containing PRELL ® shampoo of Example 7. Shampoo A contained an amine functional polysiloxane having a structure corresponding to Formula I, in which the polysiloxane had a degree of polymerization (DP=x+y+2) of 200, and which contained ten moles of amine per 100 repeat units. The amine functional polysiloxane of Shampoo A was not derivatized according to the invention, but was used as an additional "control" along with PRELL ® for purposes of comparison. Shampoo B contained an amine functional polysiloxane having a structure corresponding to Formula I, in which the polysiloxane had a degree of polymerization (DP=x+y+2) of 200, and which contained ten moles of amine per 100 repeat units. The amine functional polysiloxane of Shampoo B was derivatized according to the invention with sufficient propylene carbonate to react at all of the amine sites. Shampoo C contained an amine functional polysiloxane having a structure corresponding to Formula I, in which the polysiloxane had a degree of polymerization (DP=x+y +2) of 200, and which contained ten moles of amine per 100 repeat units. The amine functional polysiloxane of Shampoo C was derivatized according to the invention with propylene carbonate at fifty percent of the amine sites. Shampoo D contained an amine functional polysiloxane having a structure corresponding to Formula I, in which the polysiloxane had a degree of polymerization (DP=x+y+2) of 200, which contained ten moles of amine per 100 repeat units. The amine functional polysiloxane of Shampoo D was derivatized according to the invention with butyrolactone at fifty percent of the amine sites and with propylene carbonate at the remaining fifty percent of the amine sites. Shampoo D contained an amine functional polysiloxane having a structure corresponding to Formula I, in which the polysiloxane had a degree of polymerization (DP=x+y +2) of 200, and which contained ten moles of amine per 100 repeat units. The amine functional polysiloxane of Shampoo E was derivatized according to the invention with butyrolactone at fifty percent of the amine sites.

EXAMPLE 11

Dark brown "virgin" European human hair was used for testing the shampoos of Examples 7-10. A master hand of hair about eight inches in length was subdivided into a series of individual hair tresses. Each tress weighed about 2.5 grams. The top one inch portion of the hair tress was trimmed and glued to a 2"×2" plastic tab using DUCO CEMENT ®. The cement was allowed to dry, and the hair tress was combed and trimmed to a length which allowed six inches of hair to extend below the bottom of the plastic tab. Each "virgin" tress was rinsed for thirty seconds with forth degree Centigrade tap water. The tress was shampooed and lathered with two milliliters of a fifty percent solution of PRELL ® shampoo for sixty seconds by stroking the tress downwardly. The tress was rinsed for sixty seconds with tap water. Excess water was removed from the tress by passing the tress between the index and middle fingers. Instead of employing a commercial brand shampoo for treating the "virgin" tress, there may be substituted by a blank shampoo prepared by combining 450 grams of ammonium lauryl sulfate (STANDAPOL A—30 percent active) with 450 grams of distilled water. The tress was hand combed, and evaluated using the INSTRON "WET" and the INSTRON "DRY" COMBING procedures.

EXAMPLE 12

INSTRON COMBING is an industry recognized test for determining hair conditioning by the ease of wet combing and the ease of dry combing. The test employs an INSTRON strain gauge which is equipped to measure the force required to comb the hair. Conditioning performance is based on the ability of a particular hair treating formulation such as a shampoo or a hair conditioner to reduce the force required to comb the hair with the INSTRON strain gauge. The force is reported as Average Combing Load (ACL). The lower (ACL) value, the better is the conditioning effect imparted by the formulation being tested. Typically, (ACL) base lines are initially established with "untreated" tresses. The Average Combining Load is defined as the area under the force curve divided by the length or distance traveled by the INSTRON comb. This number is reported in grams of kilograms of force. The effectiveness of a treatment is the percent change in (ACL) after treatment, and this value is calculated as % Change ACL=treated hair ACL−untreated hair ACL×100-%/untreated ACL. An effective treatment is a negative number. A positive number indicates that the hair is more difficult to comb than in its untreated state.

EXAMPLE 13

For tests involving a conditioning shampoo, the hair tress is rinsed with tap water at 40° C. for thirty seconds. The test shampoo is applied to the tress in the amount of 0.5 milliliters, and lathered for thirty seconds by stroking the tress downwardly. The tress is rinsed for thirty seconds with 40° C. tap water, and 0.5 milliliters of the test shampoo are applied to the tress for a second time, and lathered for thirty seconds by stroking the tress downwardly. The tress is rinsed for thirty seconds with 40° C. tap water, and excess water is removed by passing the tress between the index and middle fingers. For tests involving a hair conditioner, the hair tress is rinsed with tap water at 40° C. for thirty seconds. The test conditioner is applied to the tress in the amount of one milliliter, and the tress is stroked for thirty seconds. The tress is rinsed for thirty seconds with 40° C. tap water, and excess water is removed by passing the tress between the index and middle fingers.

EXAMPLE 14

According to the INSTRON WET COMBING method, each hair tress is soaked for 15-30 minutes in distilled water. Excess water is removed by passing the tress through the index and middle fingers. The tress is untangled by combing the tress by hand three times. The tress is retangled by dipping the tress in distilled water three times, and excess water is removed by passing the tress through the index and middle fingers twice. The tress is placed on a hanger and INSTRON combed. The results of the INSTRON WET COMBING test conducted with the shampoos of the present invention are shown below in Table 2.

EXAMPLE 15

According to the INSTRON DRY COMBING method, each hair tress is stored overnight in a constant environment to normalize the water content of the hair. The tress is untangled by combing the tress by hand three times. The tress is retangled by swirling the tress three times clockwise, and three times counter-clockwise. The tress is placed on a hanger and INSTRON combed. The results of the INSTRON DRY COMBING test conducted with the shampoos of the present invention are shown below in Table 3.

TABLE 2

| INSTRON WET COMBING | |
|---|---|
| Shampoo Applied | Percent Change (ACL) |
| PRELL ® | 113 |
| Silicone Shampoo A | 184 |
| Silicone Shampoo B | 60 |
| Silicone Shampoo C | 52 |
| Silicone Shampoo D | −9 |
| Silicone Shampoo E | 72 |

TABLE 3

| INSTRON DRY COMBING | |
| --- | --- |
| Shampoo Applied | Percent Change (ACL) |
| PRELL ® | 23 |
| Silicone Shampoo A | −26 |
| Silicone Shampoo B | −35 |
| Silicone Shampoo C | −47 |
| Silicone Shampoo D | −27 |
| Silicone Shampoo E | −32 |

It can be seen in Tables 2 and 3, that the silicone shampoos containing the derivatized amine functional polysiloxanes of the present invention, achieved a significantly better rating under both INSTRON tests; in comparison to the commercial non-silicone containing PRELL ® shampoo, and Silicone Shampoo A which contained the amine functional polysiloxane that had not been derivatized.

While the invention has been described in terms of a shampoo composition, it should be understood that the derivatized amine functional polysiloxanes can be delivered to the hair in other forms, such as a hair conditioning products, combination shampoo/conditioner two-in-one formulations, solutions, rinses, colorants, hairstyling preparations including setting lotions and hairsprays, and permanent wave preparations.

Other variations and modifications may be made in the compounds, compositions, and methods, described herein without departing from the essential features and concepts of the present invention. The forms of the invention described herein are exemplary only, and are not intended as limitations on the scope of the invention as defined in the appended claims.

That which is claimed is:

1. In a method of conditioning hair by applying to the hair an effective amount of a composition which includes a hair conditioning agent, the improvement in hair conditioning comprising applying to the hair a composition having from 0.5 to 5.0 percent by weight of a hair conditioning agent which is a derivatized amine functional organosilicon compound selected from the group consisting of (i) a reaction product of an amine functional polysiloxane and a derivative of carbonic acid; (ii) a reaction product of an amine functional polysiloxane and a lactone; (iii) a reaction product of an amine functional silane and a derivative of carbonic acid; and (iv) a reaction product of an amine functional silane and a lactone; the amine functional polysiloxane having the formula $$R_{3-z}'Q_zSiO[R_2'SiO]_x[R^aQSiO]_ySiQ_zR_{3-z}'$$

wherein $R'$ denotes an alkyl group of 1 to 4 carbons of a phenyl group with the proviso that at least 50 percent of the total number of $R'$ groups are methyl; $R^a$ is $R'$ or an alkoxy group; Q denotes an amine functional substituent of the formula —$R''Z$ wherein $R''$ is a divalent alkylene radical of 3 to 6 carbon atoms and Z is a monovalent radical selected from the group consisting of —$NR_2'''$, and —$NR'''(CH_2)_nNR_2'''$; wherein $R'''$ denotes hydrogen or an alkyl group of 1 to 4 carbons, and n is a positive integer having an value of from 2 to 6; z has a value of 0 or 1; x has an average value of 15 to 3000; y has an average value of 0 to 100 when z is 1, y has an average value of 1 to 100 when z is 0; with the proviso that in all cases y has an average value that is not greater than one tenth the average value of x; the amine functional silane having the formula $$(RO)_{3-a}R_aSiR'NHR''$$

in which R is an alkyl group having one to four carbon atoms; $R'$ is an alkylene group having three to eighteen carbon atoms; $R''$ is selected from the group consisting of a hydrogen atom, hydrocarbon radicals free of aliphatic unsaturation having one to six carbon atoms, and aminoalkyl radicals having two to six carbon atoms; and a has a value of zero to one, the derivative of carbonic acid being a compound selected from the group consisting of ethylene carbonate and propylene carbonate; and the lactone being a compound selected from the group consisting of propiolactone, butyrolactone, valerolactone, and caprolactone.

2. A method according to claim 1 in which the amine functional silane is a compound having a formula selected from the group consisting of $(CH_3O)_3Si(CH_2)_3NHCH_2CH_2NH_2$, $(CH_3O)_3SiCH_2CH_2CH_2NH_2$, $(C_2H_5O)_3SiCH_2CH_2CH_2NH_2$, and $(CH_3O)_3SiCH_2CH(CH_3)CH_2NHCH_2CH_2NH_2$.

3. In a composition for conditioning hair which includes a hair conditioning agent as an ingredient, the improvement comprising a composition having a hair conditioning agent which is a derivatized amine functional organosilicon compound selected from the group consisting of (i) a reaction product of an amine functional polysiloxane and a derivative of carbonic acid; (ii) a reaction product of an amine functional polysiloxane and a lactone; (iii) a reaction product of an amine functional silane and a derivative of carbonic acid; and (iv) a reaction product of an amine functional silane and a lactone; the amine functional polysiloxane having the formula $$R_{3-z}'Q_zSiO[R_2'SiO]_x[R^aQSiO]_ySiQ_zR_{3-z}'$$

wherein $R'$ denotes an alkyl group of 1 to 4 carbons or a phenyl group with the proviso that at least 50 percent of the total number of $R'$ groups are methyl; $R^a$ is $R'$ or an alkoxy group; Q denotes an amine functional substituent of the formula —$R''Z$ wherein $R''$ is a divalent alkylene radical of 3 to 6 carbon atoms and Z is a monovalent radical selected from the group consisting of —$NR_2'''$, and —$NR'''(CH_2)_nNR_2'''$; wherein $R'''$ denotes hydrogen or an alkyl group of 1 to 4 carbons, and n is a positive integer having a value of from 2 to 6; z has a value of 0 or 1; x has an average value of 15 to 3000; y has an average value of 0 to 100 when z is 1, y has an average value of 1 to 100 when z is 0; with the proviso that in all cases y has an average value that is not greater than one tenth the average value of x; the amine functional silane having the formula $$(RO)_{3-a}R_aSiR'NHR''$$

in which R is an alkyl group having one to four carbon atoms; $R'$ is an alkylene group having three to eighteen carbon atoms; $R''$ is selected from the group consisting of a hydrogen atom, hydrocarbon radicals free of aliphatic unsaturation having one to six carbon atoms, and aminoalkyl radicals having two to six carbon atoms; and a has a value of zero or one, the derivative of carbonic acid being a compound selected from the group consisting of ethylene carbonate and propylene carbonate; and the lactone being a compound selected from the group consisting of propiolactone, butyrolactone, valerolactone, and caprolactone.

4. A composition according to claim 3 in which the amine functional silane is a compound having a formula selected from the group consisting of $(CH_3O)_3Si(CH_2)_3NHCH_2CH_2NH_2$, $(CH_3O)_3SiCH_2CH_2CH_2NH_2$, $(C_2H_5O)_3SiCH_2CH_2CH_2NH_2$, and $(CH_3O)_3SiCH_2CH(CH_3)CH_2NHCH_2CH_2NH_2$.

5. A composition according to claim 3 in the form of a shampoo comprising (i) 3 to 30 percent by weight of an anionic surfactant; (ii) a nonionic surfactant in an amount of 2 to 10 percent by weight; (iii) water in an amount of 50 to 93 percent by weight; (iv) the derivatized amine functional organosilicon compound hair conditioning agent in an amount to provide a shampoo composition having a viscosity of 3,000 to 6,000 centistokes, and (vi) a pH adjusting amount of an acid in an amount sufficient to establish a pH of 4–7.

* * * * *